United States Patent
Buck

(10) Patent No.: US 6,389,906 B2
(45) Date of Patent: May 21, 2002

(54) DEVICE FOR DYNAMIC-MECHANICAL ANALYSIS OF SAMPLES

(75) Inventor: Reinhold Buck, Winterthur (CH)

(73) Assignee: Mettler-Toledo GmbH, Greifensee (CH)

( * ) Notice: Subject to any disclaimer, the term of this patent is extended or adjusted under 35 U.S.C. 154(b) by 0 days.

(21) Appl. No.: 09/775,190

(22) Filed: Jan. 31, 2001

(30) Foreign Application Priority Data

Feb. 3, 2000 (EP) .............................................. 00102397

(51) Int. Cl.[7] ................................................. G01N 3/20
(52) U.S. Cl. .......................................... 73/849; 73/856
(58) Field of Search .......................... 73/788, 796, 812, 73/818, 827, 841, 846, 849, 856, 860, 831

(56) References Cited

U.S. PATENT DOCUMENTS

| | | | | |
|---|---|---|---|---|
| 4,023,102 A | * | 5/1977 | Barrow et al. | 324/537 |
| 4,317,363 A | * | 3/1982 | Shen | 73/64.41 |
| 4,509,126 A | * | 4/1985 | Olig et al. | 318/561 |
| 5,269,190 A | * | 12/1993 | Kramer et al. | 73/822 |
| 5,456,118 A | * | 10/1995 | Hines et al. | 73/818 |

\* cited by examiner

Primary Examiner—Max Noori
(74) Attorney, Agent, or Firm—Friedrich Kueffner

(57) ABSTRACT

A dynamic-mechanical analysis device has a support with upright longitudinal axis. An electro-mechanical transducer introduces a mechanical force along a linear force transmission path parallel to the longitudinal axis into holder parts of a sample holder for receiving the sample which are deflectable along the force transmission path. The introduced mechanical force is coupled to the first holder part and the reaction force is supported on the second holder part. A measuring device measures the deflection of the holder parts relative to one another. An adjusting device with connector part is connected to the force transmission path and is adjustable transverse to the longitudinal axis along first and second spatial axes perpendicular to one another. It has a first carriage slidable along the first spatial axis, a pivot frame slidable on the first carriage, and a second carriage slidable on the pivot frame along the second spatial axis. The carriages have first and second cylindrical guiding surface segments with cylinder axes parallel to the spatial axes, respectively. The pivot frame is seated on the first cylindrical guiding surface segment, and the connector part is seated on the second cylindrical guiding surface segment.

19 Claims, 11 Drawing Sheets

DEVICE FOR DYNAMIC-MECHANICAL ANALYSIS OF SAMPLES

BACKGROUND OF THE INVENTION

1. Field of the Invention

The invention relates to a device for dynamic-mechanical analysis of samples, wherein on a rigid support with uprightly aligned longitudinal axis along a linear force transmission path extending parallel thereto the following are arranged: an electromechanical transducer, connected to the force transmission path, for introducing a mechanical force corresponding to an electrical drive signal; a sample holder with two holding parts which are deflectable relative to one another along the force transmission path, wherein the force introduced by the transducer is coupled to one of them and a first area of the sample can be fastened thereto, and wherein the reaction force opposite to the introduced force is supported on the other one and a second area of the sample, spaced from the first area, can be fastened thereto; a device for measuring the deflection, caused by the introduced force, of the two holding parts relative to one another; and an adjusting device with a connector part connected to one end of the force transmission path which is adjustable transverse to the longitudinal axis along a first spatial axis and along a second spatial axis perpendicularly arranged to the first spatial axis.

2. Description of the Related Art

With such devices material properties of samples, for example, their modulus of elasticity, are examined by periodic force action on the sample. In this connection, it is desirable to perform the test with high precision across a broad frequency range. In this respect, however, there is the problem of undesirable vibrations, in particular, in the range of high frequencies. Moreover, for achieving a good measuring precision, a precise adjustment relative to the linear force transmission path is required.

SUMMARY OF THE INVENTION

It is an object of the present invention to improve a device of the aforementioned kind with respect to the measuring precision and the usable frequency range.

In accordance with the present invention, this is achieved in that the adjusting device comprises a first carriage which is slidably guided along the first spatial axis as well as a pivot frame, which is slidably guided on the first carriage on a first cylindrical guiding surface segment with a first cylinder axis which is parallel to the first spatial axis, and a second carriage, which is slidably guided on the pivot frame along the second spatial axis, on which second carriage the connector part is guided on a second cylindrical guiding surface segment with a second cylinder axis which is parallel to the second spatial axis.

With the inventive embodiment of the adjusting device, not only the point of attack of the introduced force on the sample holder can be adjusted in a plane which extends perpendicularly to the longitudinal axis, but also the direction of the introduced force. In this connection, the connector part is subjected to such a guiding action by the two cylindrical guiding surface segments that it is focused in its longitudinal direction on the two cylinder axes. The adjustability of the spatial angle achievable in this way and the transverse adjustments taking place along the two spatial axes are independently adjustable relative to one another within the frame of the required adjusting range and precision. A further advantage of the adjusting device embodied according to the invention resides in its compact configuration and minimal space requirement.

Expediently, it is suggested that the first and the second cylinder axes intercept one another. Such a selection of the curvature radii and spatial arrangement of the two guiding surface segments favor the degree of independence of the transverse adjustment and spatial angle adjustment. This contributes significantly to an increase of the operating convenience.

According to an expedient embodiment, it is suggested that, for adjusting in the direction of the first spatial axis, the first carriage is guided in a stationary frame-shaped lower housing part in which a first threaded spindle is rotatably supported which extends axially in the first spatial direction and engages a thread of the first carriage. In this connection, the degree of adjustment in the first spatial direction is determined by the pitch of the first threaded spindle and the respective magnitude of its rotation.

Another expedient embodiment is characterized in that the first cylindrical guiding surface segment is formed by two circular disc segments provided on two end faces, extending transversely to the first spatial axis, of the first carriage, between which the pivot frame is arranged and supported on recesses with a complementary configuration provided on its corresponding end faces. In this way, the construction height in the longitudinal axis is kept particularly small.

With respect to the adjustability in the second spatial direction, the device can be expediently configured such that the second carriage is guided in that pivot frame in which a second threaded spindle is rotatably supported and extends axially in the second spatial direction and engages a thread of the second carriage. In this connection, the pitch of the second threaded spindle and the respective rotation imparted thereon determine the adjustment in the second spatial direction.

Moreover, it is expedient, in particular, with respect to a minimal construction height, to design the device such that the second cylindrical guiding surface segment is formed by two cylindrical mantle segments formed on two end faces, extending transverse to the second spatial direction, of the second carriage on which cylindrical mantle segments the connector part is supported by means of gliding surfaces complementarily embodied thereto.

For the total configuration of the device it is also advantageous that the connector part has a projection extending in the longitudinal direction and penetrating through cutouts of the carriage and the pivot frame. In this way, the connector part with its projection is freely accessible via an end face of the adjusting device so that the connection of force transmission members acting along the force transmission path is facilitated.

For adjusting the spatial angle in a plane perpendicular to the first spatial axis, the device is expediently configured such that in a stationary upper housing part a third threaded spindle is rotatably supported which extends axially in the second spatial direction. A driver engaging the pivot frame is guided on its thread. The pitch and rotation of the third threaded spindle determines the displacement of the driver along the second spatial direction and thus the position of the pivot frame, entrained by the driver, on the first cylindrical guiding surface segment. This determines the angular adjustment in planes perpendicular to the first spatial axis.

For adjusting the spatial angle in planes perpendicular to the second spatial axis, the device is expediently designed such that in a stationary upper housing part a fourth threaded spindle, which extends in the axial direction in the first spatial direction, is rotatably and axially slidably supported. It is coupled by a first driver with the second carriage, and a second driver is guided on its thread and engages the connector part. As a result of this coupling with the second carriage, the fourth threaded spindle follows the adjusting movement along the first spatial axis while, as a result of its rotation, the second driver is correspondingly moved according to its pitch along the first spatial axis, and the connector part coupled with the second driver is thereby moved correspondingly on the second cylindrical guiding surface segment so that the spatial angle is adjusted in the planes parallel to the second spatial axis.

Within the context of the invention it is furthermore provided that on the parts, guided on the threads of the threaded spindles, indicator pins are secured which extend parallel to the threaded spindles. Since the transverse adjustment of the connector parts along the first and second spatial axes is determined by the position of the first and second carriages on the threads of the first and second threaded spindles and the spatial angle adjustment by the position of the drivers on the threads of the third and fourth threaded spindles, the indicator pins secured on these parts show the operator relative to the corresponding threaded spindles the adjustments of the transverse position and of the spatial angles.

Another contribution to the solution of the object is achieved, in particular, for a device of the aforementioned kind in that the sample holder has a housing with a receiving chamber, extending through the housing longitudinally to a transverse axis which is oriented transverse to the longitudinal axis, for a three-part insert whose central part, when viewed in the direction of the transverse axis, forms the first holder part and is positive-lockingly supported in a ring, which is arranged with play in the receiving chamber, and whose lateral parts on both sides of the central part form the second holder part and are supported positive-lockingly in the receiving chamber. Also provided are an opening for penetration by a force transmission member extending on the longitudinal axis and connected to the ring and a connecting area positioned opposite the opening, when viewed in the direction of the longitudinal axis, for a member serving to receive the reaction force.

This configuration of the sample holder is, on the one hand, advantageous with respect to the oscillation behavior and the stability requirements. On the other hand, it provides the ability for receiving differently designed samples and is easy to handle. In particular, these advantages are achieved when the central part and the two lateral parts are formed as cylindrical discs with circular end faces extending radially relative to the transverse axis. This configuration is suitable, in particular, for examining samples under shearing load. In this connection, the samples are clamped between the circular end faces of the central part and of the two lateral parts.

An embodiment which is particularly suitable for strip-shaped samples is configured such that the insert has a sample receiving chamber formed in its central part, a clamping gap extending from the sample receiving chamber radially outwardly relative to the transverse axis, and a rigid rod penetrating the sample receiving chamber in the direction of the transverse axis at a location radially spaced from the clamping gap, the rod with its ends being supported in recesses of the two lateral parts. In this case, the strip-shaped sample can be wound about the rigid rod and can be clamped with its free ends in the clamping gap. The sample is then tested with respect to tension.

An embodiment which is expedient for the pressure excitement of samples resides in that the insert has a sample receiving chamber formed in its central part, a support surface provided within the sample receiving chamber for radially supporting a sample relative to the transverse axis, and a counter abutment penetrating the sample receiving chamber in the direction of the transverse axis at a location radially spaced from the support surface and supported with its ends in recesses of the two lateral parts. In this case, a block-shaped or rod-shaped sample is clamped between the support surface and the counter abutment and the pressure forces introduced into the sample.

A measure which is particularly beneficial for manipulating the sample holder resides in that in the central part and the two lateral parts centering bores, aligned with one another in the direction of the transverse axis, are formed for receiving centering pins. By means of the centering pins the two lateral parts and the central part can be centered relative to one another and fixed, which facilitates the assembly of the sample holder when inserting different types of samples.

According to a further proposal of the invention, a contribution to the solution of the object is achieved, in particular, for a device of the aforementioned kind, in that the support is formed in the form of a tubular body surrounding the force transmission path with the transducer, the sample holder, the measuring device, and the adjusting device and having an access opening provided in the area of the sample holder.

The tubular body provided as a carrier enables a particularly bending-resistant configuration. This results in a beneficial oscillation behavior under the excitation force which is introduced into the force transmission path and whose reaction force is received by the carrier.

The preferred embodiment resides in that in the area of the sample holder two tempering chamber halves are provided which are slidable along a transverse axis extending transverse to the longitudinal axis between a closed position, in which they surround the sample holder, and an open position, in which the sample holder is exposed. In the open position the two tempering chamber halves can additionally be pivoted to the rear and top in order to provide an even better accessibility of the sample chamber. It is often desirable to perform the dynamic-mechanical analysis under different temperatures. The two tempering chamber halves produce in their closed position the desired temperature environment for the sample. On the other hand, in the open position the sample holder with the sample is easily accessible, in particular, for an exchange. Depending on the desired temperature, the two tempering chamber halves can be heated as well as cooled.

In this connection, a particularly expedient configuration is characterized in that the tempering chamber halves are arranged on two lateral arms supported on the tubular body.

Further features, details, and advantages result from the following description in which the invention is described in detail with the aid of one embodiment with reference to the drawing.

DESCRIPTION OF THE PREFERRED EMBODIMENTS

Figure 1:
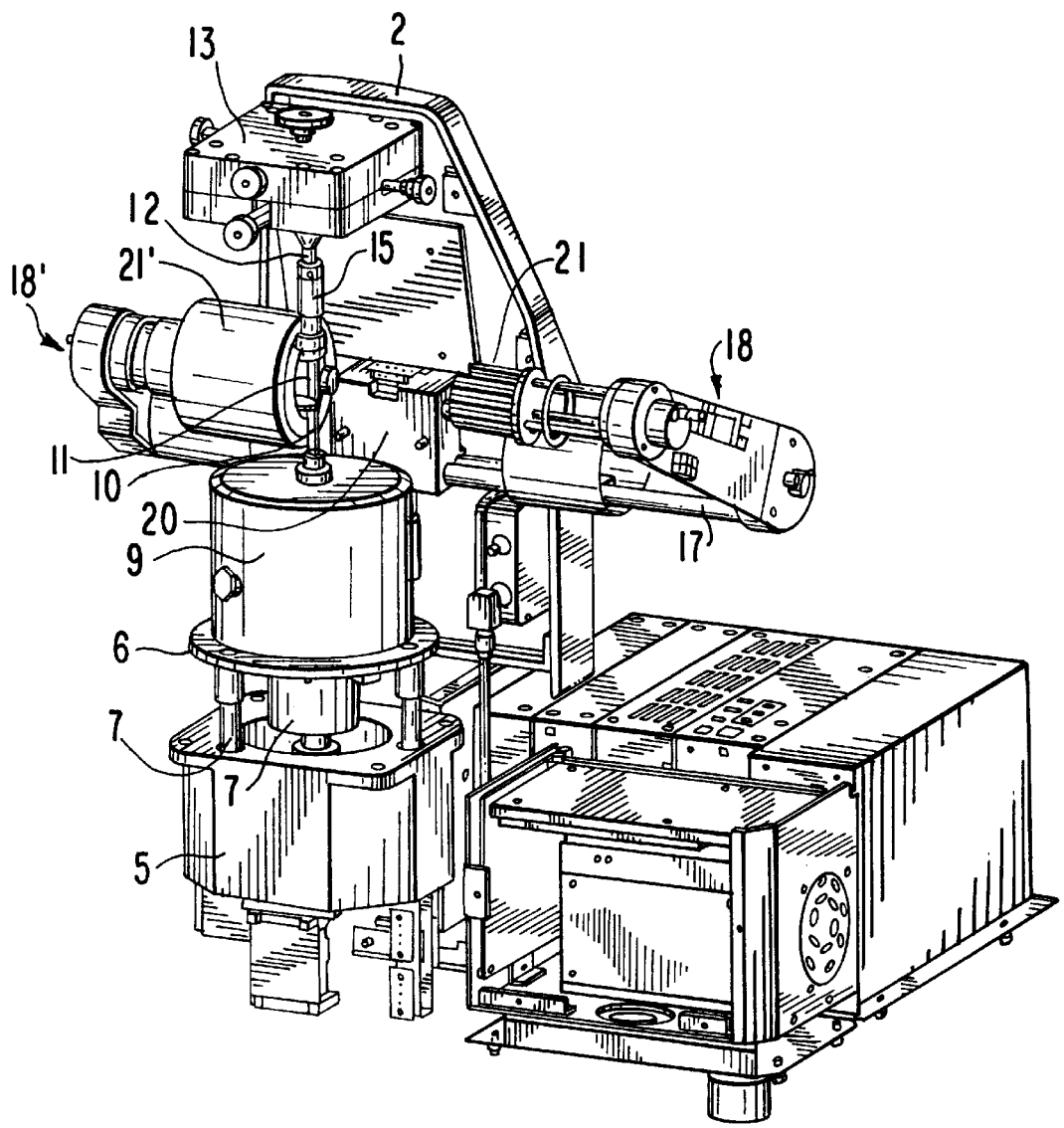
FIG. 1 shows a view of the inner configuration of the device for dynamic-mechanical analysis of samples, wherein, for allowing a view into the interior, the surrounding tubular carrier has been removed.
Figure 2A:
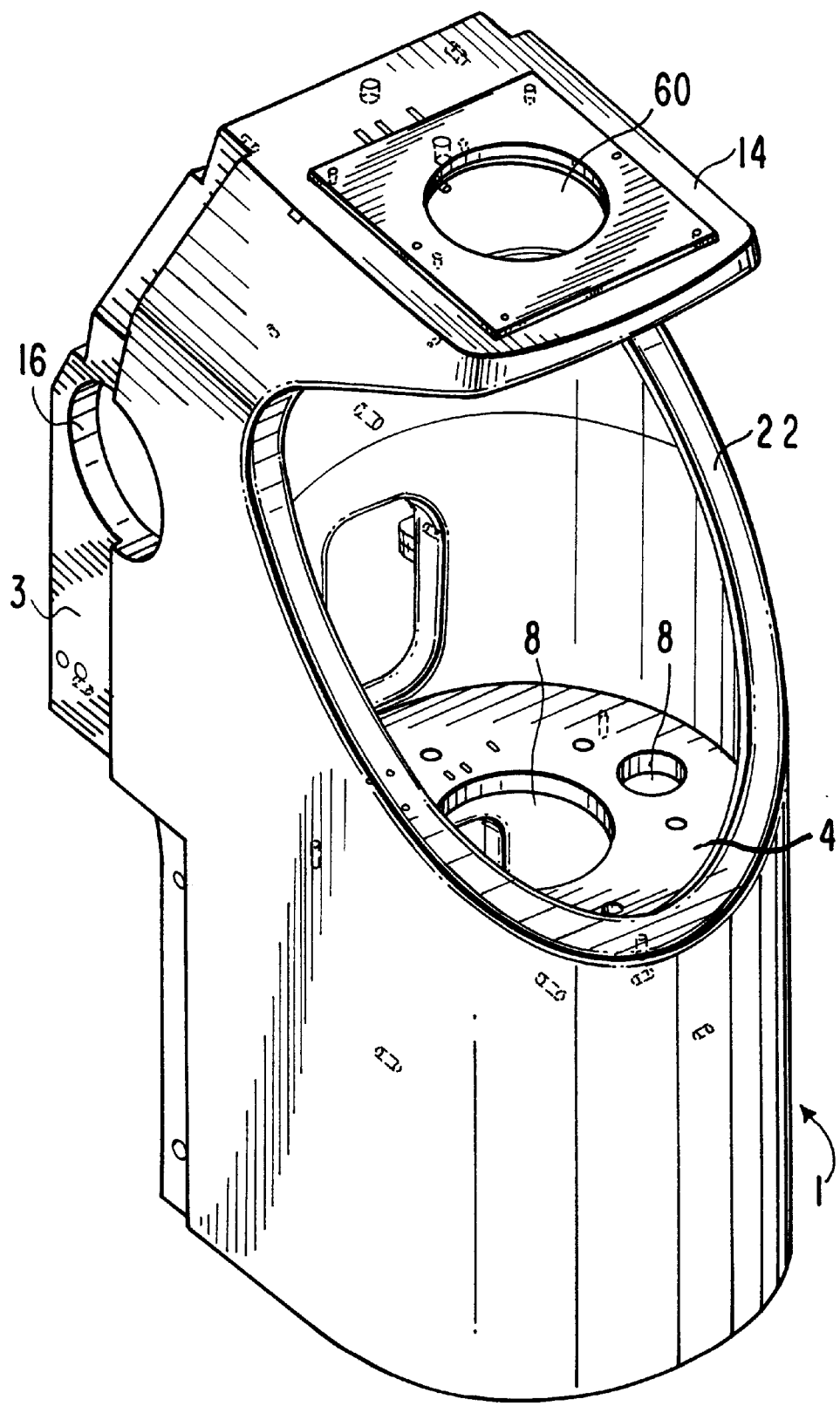
FIGS. 2a, 2b show perspective views of the tubular carrier from the front and from the rear.
Figure 2B:
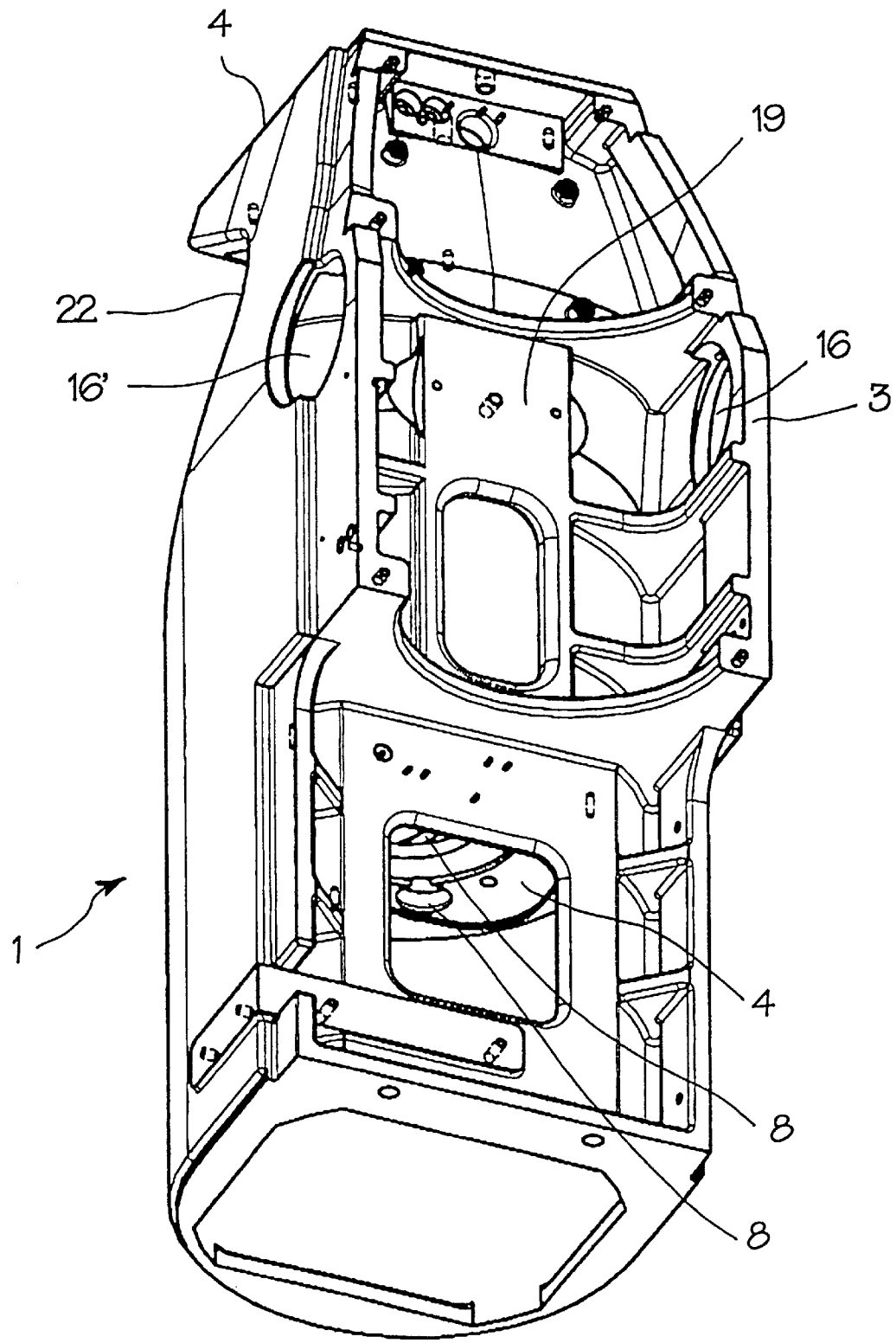

A rigid support in the form of a tubular body 1 illustrated in FIGS. 2a and 2b serves as a carrier for the essential components of the device for dynamic-mechanical analysis of samples. This device is illustrated in FIG. 1 without the supporting tubular body 1 so that the components that are surrounded in the assembled state by the tubular body 1 are visible. In FIG. 1 only a rear cover 2 is illustrated additionally which does not impair the view, wherein the cover 2 closes a rear projection 3 of the tubular body 1 in the assembled state.

In the assembled state of the device the tubular body 1 is positioned upright with regard to its longitudinal axis.

The interior of the tubular body 1 has a transverse wall 4 approximately at the center of its longitudinal extension which extends perpendicularly to the longitudinal axis. At their downwardly positioned side, an actuator member 5 for the lifting table 6 movable in the direction of the longitudinal axis is provided. The lifting table 6 is coupled for actuation with the actuator member 5 by guide and push members extending parallel to the longitudinal axis and penetrating through corresponding cutouts 8 of the transverse wall 4.

On the lifting table 6 an electromechanical transducer 9 is supported. The transducer 9 can be, for example, in the form of an oscillation coil which is arranged in the magnetic like a loudspeaker. Upon introduction of an electrical drive signal, the oscillation coil produces a corresponding mechanical force in the direction of the longitudinal axis.

This mechanical force is transmitted by a rod-shaped coupling member 10, extending in the direction of the longitudinal axis, onto a sample holder 11 of which different embodiments are illustrated in FIGS. 5 through 10. The reaction force corresponding to the force introduced into the sample holder 11 via the coupling member 10 by the electro-mechanical transducer 9 is measured during its further course of the force transmission path extending in the longitudinal direction by a force sensor 12 arranged in the force transmission path. The force sensor 12, which may be, for example, a quartz force sensor, is coupled to an adjusting device 13 which is illustrated in detail in FIGS. 3 and 4. This adjusting device 13 is supported on an upper end face 14 of the tubular body 1 extending perpendicularly to the longitudinal axis.

Between the sample holder 11 and the force sensor 12 a distance sensor 15 is arranged in the force transmission path which measures the deflections of the sample arranged on the sample holder 11 resulting from the introduced force. It may be, for example, a known inductive distance sensor in which the movement of a core in a coil is detected.

The rear projection 3 of the tubular body 1 has two openings 16, 16' which are aligned along a transverse axis extending perpendicularly to the longitudinal axis. Support rods 17 of lateral arms 18, 18', arranged on both sides of the tubular body 1, extend through these openings parallel to this transverse axis. The support rods 17 are slidably supported in the direction of the transverse axis in a holder 20 which is secured on a fastening wall 19 within the rear projection 3. The holder 20 can be provided with a motor effecting the transverse movement of the support rods 17.

The lateral arms 18, 18' extend from the ends of the support rods 17 facing away from the tubular body 1 transverse to the support rods 17 into the area of an imaginary axis extending parallel to the support rods 17 and through the sample holder 11. In this area each of the two lateral arms 18, 18' has a tempering chamber half 21, 21'. In the illustrated embodiment, the tempering chamber halves 21, 21' are formed cylindrically about the imaginary transverse axis extending through the sample holder 11 and are open at their radial end faces facing one another. Adjacent to these end faces, the cylinder mantles are provided with recesses complementary to the coupling member 10 and to the distance sensor 15. Accordingly, they can be placed against one another with their end faces so that they surround the sample holder 11 but, at the same time, allow the coupling member 10 and distance sensor 15 connected thereto to penetrate. The slidable support of the support rods 17 in the holder 20 makes possible the displacement of the tempering chamber halves 21, 21' between their closed position, in which they surround the sample holder 11, and their open position, in which the sample holder 11 is exposed. Moreover, the two tempering chamber halves can be pivoted away by rotation of the lateral arms to the rear and top.

In order to make access of the two tempering chamber halves 21, 21' to the sample holder 11 possible, an access opening 22 of a sufficient size is formed in the front side opposite the rearward projection 3. This access opening 22 opens like a mouth to the front side facing the operator and facilitates at the same time manipulation of the sample holder 11, in particular, when inserting it into the device and removing it from the device.

Figure 3:
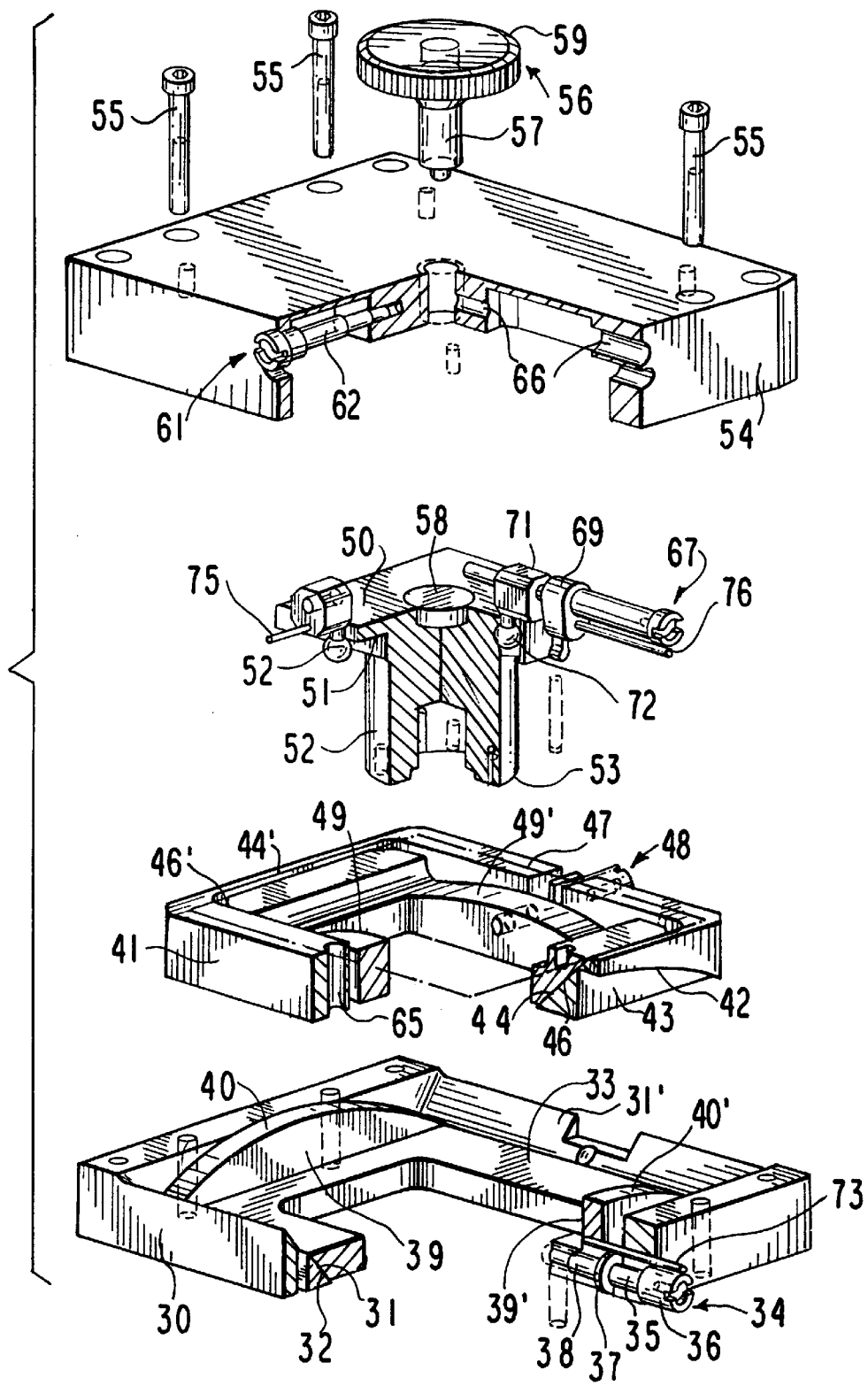
FIG. 3 is an exploded view of an adjusting device illustrated in the top half of FIG. 1.
Figure 4:
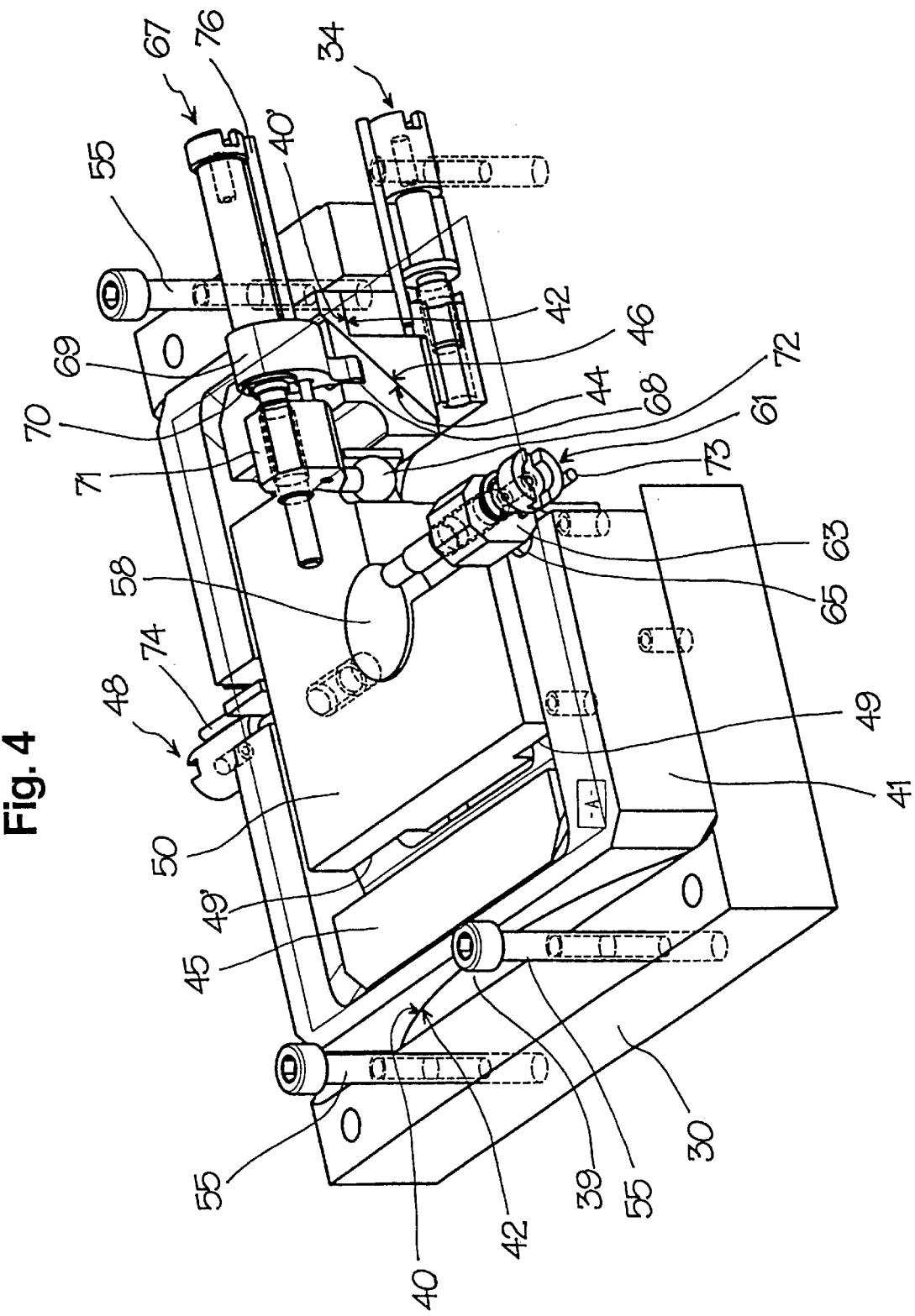
FIG. 4 shows the adjusting device of FIG. 3 in the assembled state with removed outer housing part.

From the exploded view of FIG. 3 and the partial illustration of the assembled state in FIG. 4 it can be seen that the adjusting device 13 has a flat frame-shaped lower housing part 30 whose frame plane, when mounted in the device, extends according to FIG. 1 transversely to the longitudinal axis. In FIG. 3 the right front corner is cut away for the purpose of illustration. This shows that, at the inner sides of two oppositely positioned frame legs extending parallel to the first spatial direction, linear gliding guides 31, 31' are provided whose surface normal is slanted relative to the longitudinal axis, for example, by 45°. On these gliding guides 31, 31', complementary formed gliding surfaces 32 of a first carriage 33 arranged within the frame-shaped lower housing part 30 are guided in a slidable manner. In one of the frame legs of the lower housing part 30 extending transversely to the gliding guides 31, 31', a threaded spindle 34 is rotatably arranged with its threadless cylindrical shaft portion 35 but is axially non-slidably supported in that it is axially supported with one end by a shoulder provided on the head 36 at the outer side of the frame leg and with the other end by a shoulder formed by a ring disc 37 at the inner side of the frame leg. A shaft portion 38 which extends from the side of the annular disc 37 facing away from the frame leg is provided with a thread which meshes with a corresponding counter thread of the bore of the first carriage 33. In this way, the first carriage 33 is adjusted in the first spatial direction by rotation of the threaded spindle 34.

On the two end faces of the first carriage 33 extending transversely to the first spatial axis, circular disc segments 39, 39' are formed which, in the mounted state of FIG. 1, are curved upwardly in the direction of the longitudinal axis and whose radial planes extend parallel to the longitudinal axis as well as transverse to the frame plane of the lower housing part 30. The radial edges of the circular disc segments 39, 39' form in this way cylinder segment-shaped guiding surfaces 40, 40' on which a pivot frame 41 with guide surfaces 42 complementary thereto is slidingly supported. These guiding surfaces 42 are formed by shoulders in corresponding legs of the pivot frame 41 whose peripheral surfaces 43, perpendicular to the guiding surfaces 42, secure non-slidably the pivot frame 41 between the circular disc segments 39, 39' in the first spatial direction.

The frame legs of the pivot frame 41 provided with the guiding surfaces 42 extend parallel to a second spatial direction extending perpendicularly to the first spatial direction. At their inner sides, gliding guides 44, 44', embodied similar to the gliding guides 31, 31' of the lower housing part 30, are formed on which a second carriage 45, arranged in the interior of the pivot frame 41, is slidably guided in the second spatial direction with gliding surfaces 46, 46' complementary thereto.

Similar to the adjustment of the first carriage 33 in the lower housing part 30 by means of the threaded spindle 34, a second threaded spindle 48 extending in the second spatial direction is rotatably and axially non-slidably supported in a frame leg 47 extending perpendicularly to the second spatial direction of the pivot frame 41. The shaft portion of the second threaded spindle provided with the thread meshes with a thread in the second carriage 45 which is complementary thereto. In this way, the rotation of the second threaded spindle 48 adjusts the second carriage 45 in the second spatial direction.

On two end faces of the second carriage 45 extending perpendicularly to the second spatial direction, cylinder segment-shaped guiding surfaces 49, 49' are formed so as to extend upwardly in the direction of the longitudinal axis. A connector part 50 is supported thereon with gliding surfaces 51 of a complementary curvature. The two carriages 33 and 45 as well as the lower housing part 30 and the pivot frame 41 have a frame shape with a free inner cross-section. A cylindrical projection 52 formed on the connector part 50 with a cylinder axis parallel to the longitudinal axis penetrates the inner cross-section so that, in the assembled state, the downwardly pointing radial end face 53 of the projection 52 is exposed at the underside of the lower housing part 30.

FIG. 4 shows a state in which the parts of the exploded view of FIG. 2 are assembled such that the first carriage 33 with its circular disc segments 39, 39' at the end faces is placed onto the gliding guides 31, 31' of the lower housing part 30. Moreover, the pivot frame 41 is placed with its cylindrical segment-shaped guiding surfaces 42 onto the cylinder segment-shaped guiding surfaces 40, 40' of the first carriage 33. A second carriage 45 is inserted into the pivot frame 41. The right lower portion broken away in FIG. 4 for illustration purposes shows in cross-section the contact between one of the gliding guides 44 of the pivot frame 41 and one of the gliding surfaces 46 of the second carriage 45. Finally, the connector part 50 is visible on the cylinder segment-shaped guiding surfaces 49, 49' of the second carriage 45. Moreover, FIG. 4 shows the two threaded spindles 34 and 48, one being rotatably supported in the lower housing part 30 and the other in the pivot frame 41.

Onto the assembled state illustrated in FIG. 4, the upper housing part 54, illustrated in the upper half of the exploded view of FIG. 3, is placed and secured by threaded bolts 55 extending parallel to the longitudinal direction on the lower housing part 30. A pressure member 56 centrally threaded into the upper housing part 54 presses with the free end face of a threaded bolt 57 extending in the longitudinal direction onto a counter abutment 58 on the connector part 50 and thus keeps the parts under axial tension relative to one another. The clamping pressure is adjustable by means of a turn knob 59 arranged at the opposite end of the threaded bolt 57.

FIG. 3 also shows that in the upper housing part 54 a third threaded spindle 61 is rotatably and axially non-slidably supported in a similar way as the first and second threaded spindles 34, 48 in the lower housing part 30 or the pivot frame 41. On the threaded shaft portion 62 of the third threaded spindle 61 extending in the second spatial direction, a driver 63 having a complementary thread is guided. The driver 63 engages with a spherical end portion 64 of a downwardly pointing projection a cylindrical bore 65 of the pivot frame 41. This can be seen, in particular, in FIG. 4 in which the third threaded spindle 61 and the driver 63 are also illustrated. When a rotation of the threaded spindle 61 is carried out, the driver is moved in the second spatial direction and entrains, by engagement of the spherical end portion 64 of its projection in the bore 65, the pivot frame 41 on the cylindrical segment-shaped guiding surfaces 40, 40' of the first carriage 33. The thus effected adjustment of the spatial angle in the plane perpendicular to the first spatial direction remains unchanged even when the pivot frame 41 is moved following an adjustment of the first carriage 33 in the first spatial direction by means of the threaded spindle 34 because then the driver 63 follows this movement by a corresponding pivot movement about the axis of the third threaded spindle 61 and, for a suitable magnitude of the frictional connection between the driver 63 and the third threaded spindle 61, the latter also follows the pivot movement of the driver 63 without this causing a relative rotation between the driver 63 and the threaded spindle 61.

FIGS. 3 and 4 also show that a fourth threaded spindle 67 is guided rotationally and axially movably in a bore 66 of the upper housing part 54, whose bore axis extends in the first spatial direction. On the fourth threaded spindle 67 a first driver 69 is rotatably but axially non-slidably mounted which engages a cutout 68 of the second carriage 45 but is axially non-slidable supported. For this purpose, the driver 69 is supported on one side on a radial shoulder of a portion of the threaded spindle 67 projecting from the upper housing part 54 and also with its opposite side on a radial disc 70 of the fourth threaded spindle 67. On the portion of the fourth threaded spindle 67 extending from the radial disc 70 inwardly and being provided with the thread, a second driver 71 is guided with a complementary thread. A spherical end portion 72 of a projection provided on the second driver 71 engages a bore of the connector part 50. In this way, the connector part 50, upon rotation of the fourth threaded spindle 67, is pulled, as a result of the movement of the second driver 71 on the fourth threaded spindle 67, across the guide surfaces 49, 49' of the second carriage 45 so that the spatial angle is adjusted in a plane which is perpendicular to the second spatial direction. At the same time, the first driver 69 coupled with the second carriage 45 ensures that the fourth threaded spindle 67 in the bore 66 follows the movement of the second carriage 45 upon adjustment in the first spatial direction by means of the first threaded spindle 34. At the same time, the first driver 69 upon adjustment of the second carriage 45 by means of the second threaded spindle 48 can follow the movement of the second threaded spindle 48 by a corresponding pivot action on the fourth threaded spindle 67 without this causing a relative rotation between the fourth threaded spindle 67 and the second driver 71 arranged thereon. As a result, the adjustment of the spatial angle in the plane perpendicular to the second spatial direction is not affected by an adjustment in the first and second spatial directions by means of the threaded spindles 34 and 48.

On the first carriage 33 and the second carriage 45 indicator pins 73 and 74, respectively, are fastened which extend parallel to the first threaded spindle 34 and the second threaded spindle 48. They extend out of the housing comprised of the lower housing part 30 and the upper housing part 54. The position of the indicator pins 73 and 74 relative to the corresponding spindle thus allows the operator to read the position of the connector part 50 relative to the first and second spatial directions.

In a similar way, on the driver 63 an indicator pin 75 is fastened with which extend parallel to the third threaded spindle 61 and is guided out of the housing parallel to the threaded spindle. This indicator pin 75 indicates the adjustment of the spatial angle in the plane perpendicular to the first spatial direction. Simultaneously, on the second driver 71 an indicator pin 76 is fastened which extend parallel to the fourth threaded spindle 67 and is guided through a through opening of the first driver 69 out of the housing. By means of the indicator pin 76 the adjustment of the spatial angle in the plane perpendicular to the second spatial direction is indicated.

Figure 5:
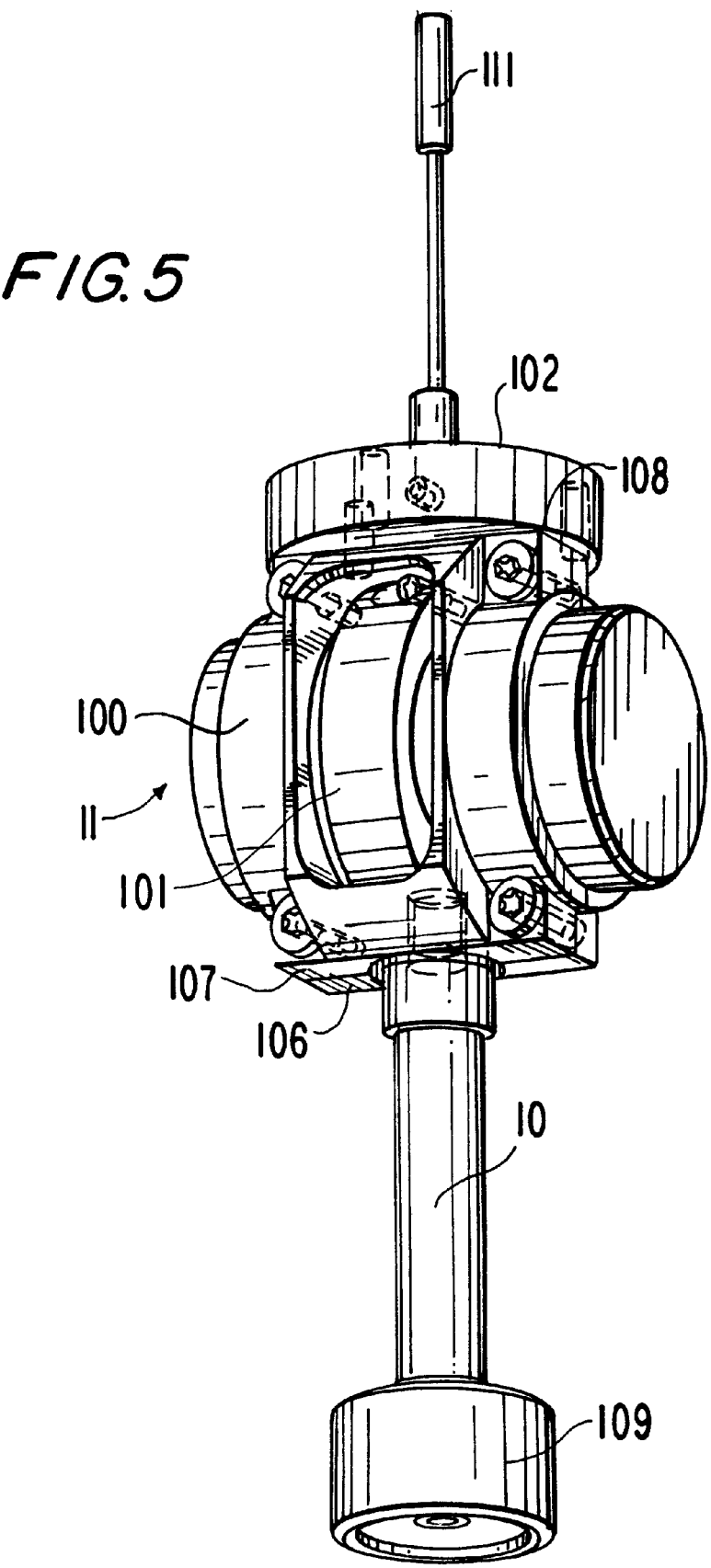
FIG. 5 is a view on a large scale of the sample holder shown in the upper area of FIG. 1.
Figure 6:
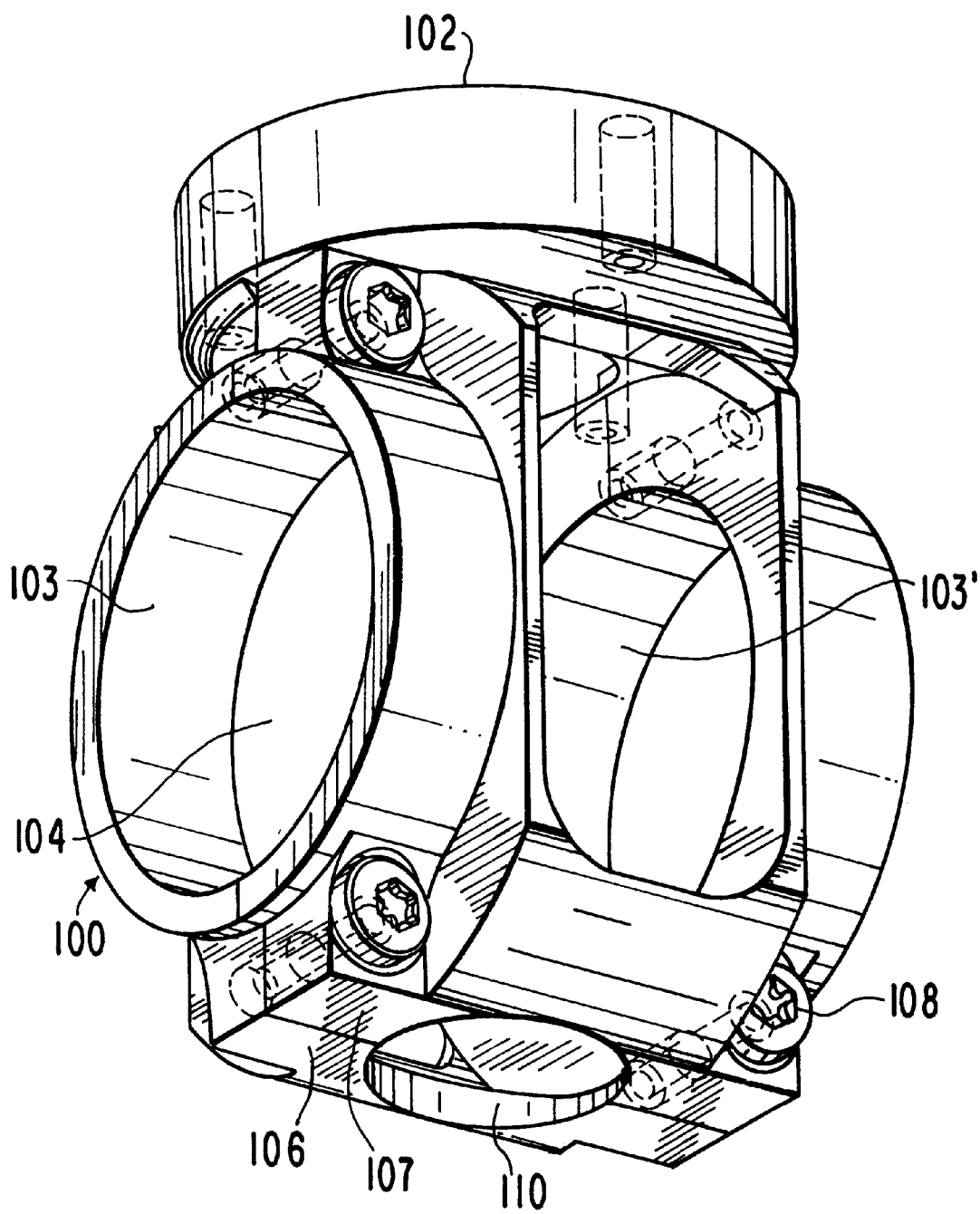
FIG. 6 is an individual representation of the housing of the sample holder of FIG. 5.
Figure 7:
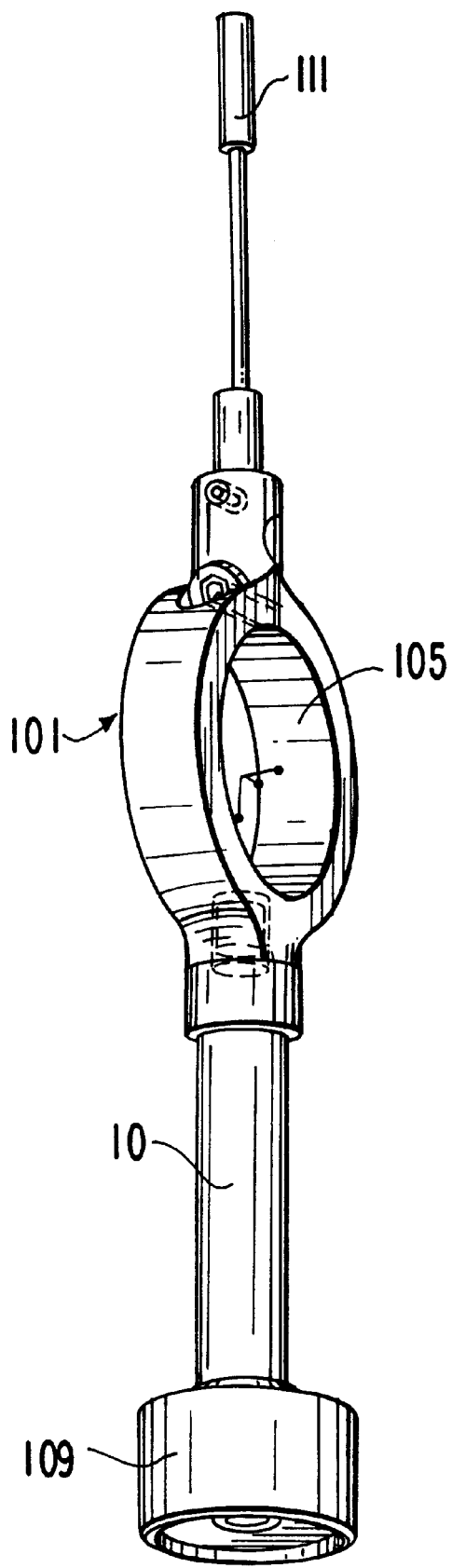
FIG. 7 is an individual representation of a ring of the sample holder of FIG. 5 arranged in the housing.

FIG. 5 shows a complete view of an embodiment of the sample holder 11 which comprises a housing 100 illustrated in FIG. 6 and a ring 101 illustrated in FIG. 7. On the housing 100, a connector flange 102 is formed which is complementary to a connector flange of the distance sensor 15 extending radially relative to the longitudinal axis. The housing 100 is fixedly connected with flange 102 by screws extending parallel to the longitudinal axis to the housing of the distance sensor 15.

A transverse axis extending transversely to the longitudinal axis forms a common cylinder axis for the two cylindrical inlet areas 103, 103' of a receiving chamber which comprises a central area 104 positioned axially between the two inlet areas and enlarged relative to the inlet areas. The ring 101 is arranged with play on all sides in the central area 104 and the ring's cylindrical inner mantle 105 has the same diameter as the two cylindrical inlet areas 103, 103'. The housing 100 is divided into two parts along a plane which is defined by the longitudinal axis and the transverse axis, wherein the two shell-shaped parts 106, 107 are connected to one another by threaded bolts 108 extending transverse to the longitudinal axis. The play available to the ring 101 within the housing 100 is of such a magnitude that in a central position of the inner mantle 105 of the ring 101 is precisely aligned with the inner mantles of the cylindrical inlet areas 103, 103'. From this center position the ring 101 can be deflected at least by the maximum deflection desirable for the dynamic-mechanical analysis of the samples without contacting the housing 100.

At the outer circumference of the ring 101, the rod-shaped coupling member 10 extending toward the electromechanical transducer 9 is secured in the radial direction. The end of the coupling member 10 facing away from the ring 101 is provided with a union nut 109 which in cooperation with a steep taper serves to connect the coupling member 10 to the transducer 9. In the housing 100 in the area which is diametrically opposite to the connecting flange 102 a through opening 110 is formed through which the coupling member 10 is guided out of the housing 100 with lateral play. The through opening 110 has positioned diametrically opposite thereto also a through opening in the connecting flange 102 through which the core 111 of the distance sensor 15, aligned with the longitudinal axis of the coupling member 10, is guided, wherein the core 111 is fastened on a location of the ring 101 which is diametrically opposite the fastening location of the coupling member 10 on the ring 101. In the assembled state the connecting flange 102 of the housing 100 is clamped with a corresponding connector flange of the tubular outer mantle of the distance sensor 15 so that the core 111, in a manner known in the art, is moveably guided axially in the cylindrical coil of the distance sensor 15.

Figure 8:
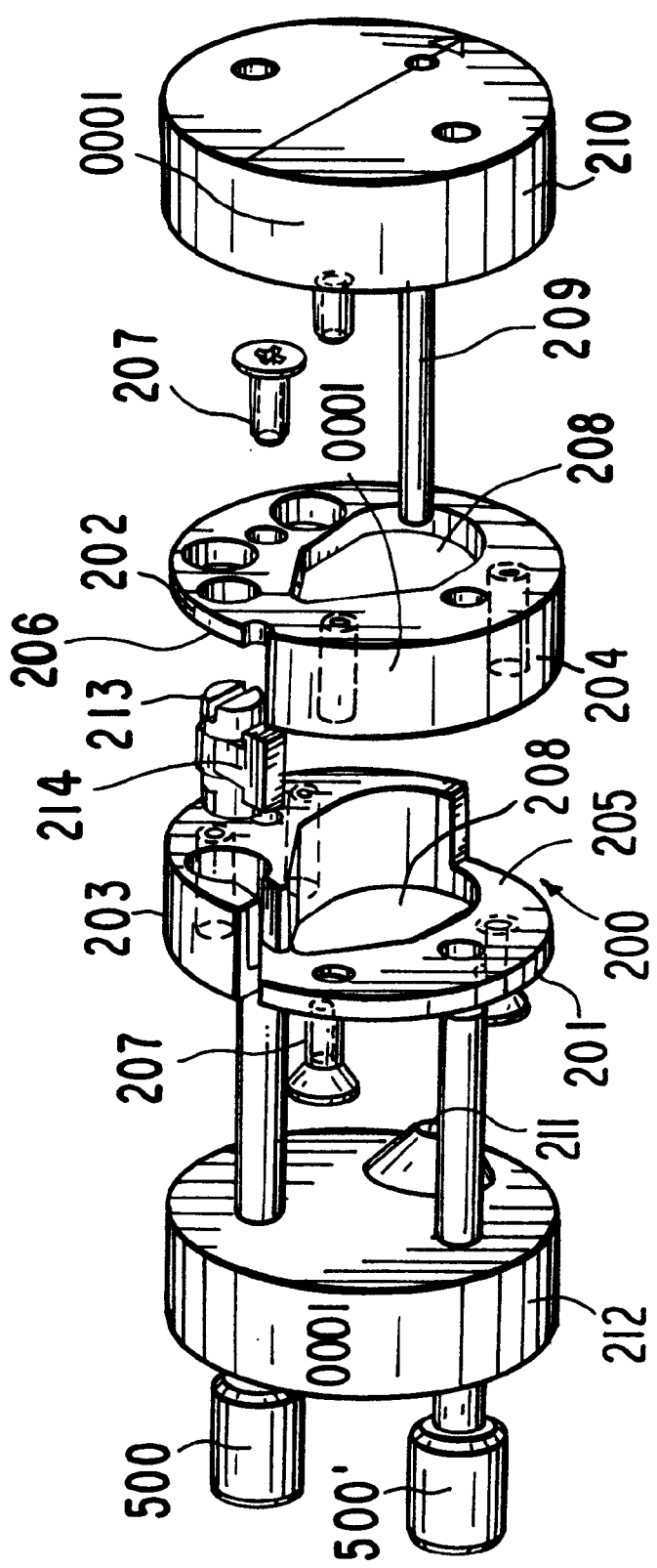
FIG. 8 shows an exploded view of a first embodiment of an insert for the sample holder of FIGS. 5 through 7.
Figure 9:
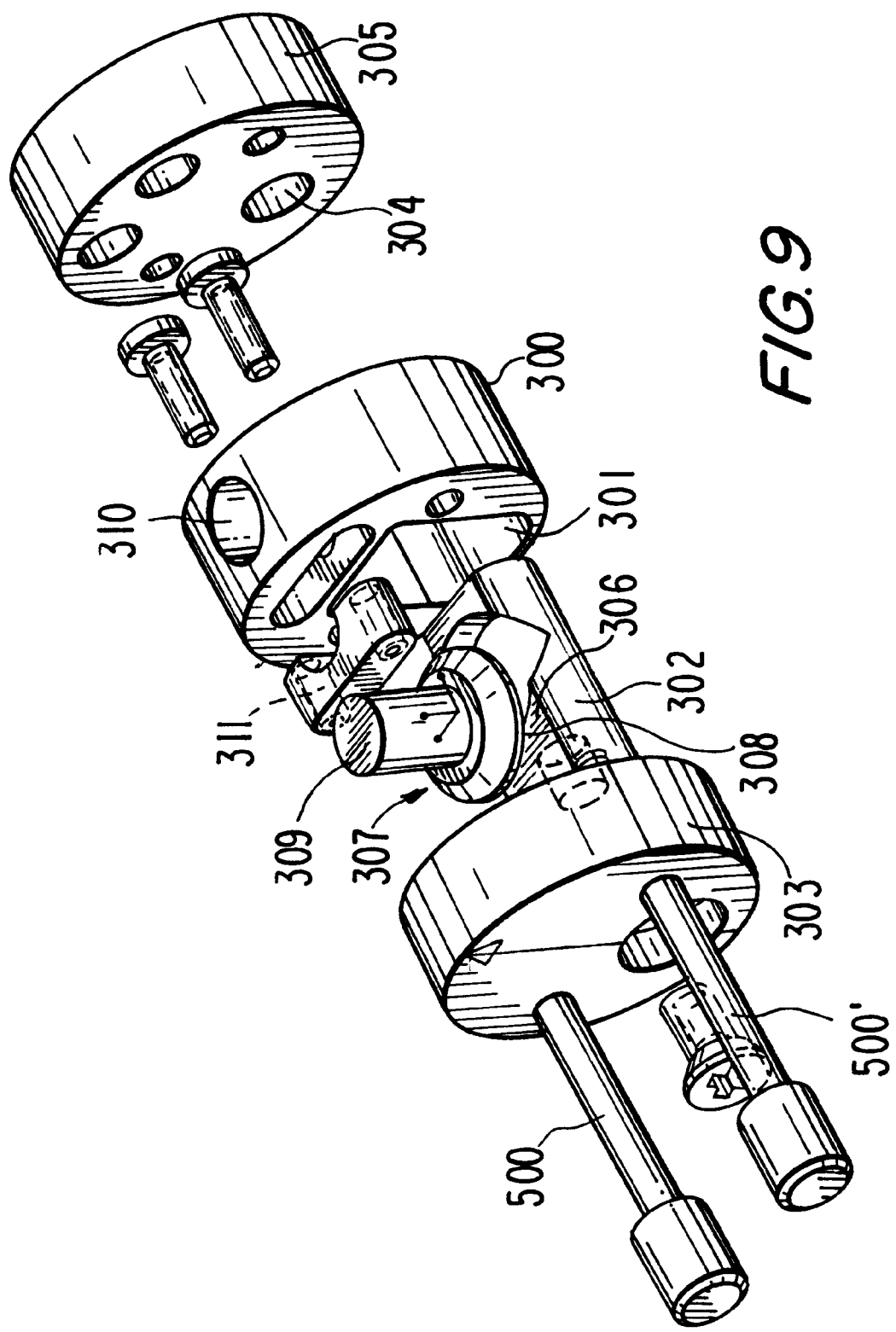
FIG. 9 is an exploded view of a second embodiment of an insert for the sample holder of FIGS. 5 through 7.
Figure 10:
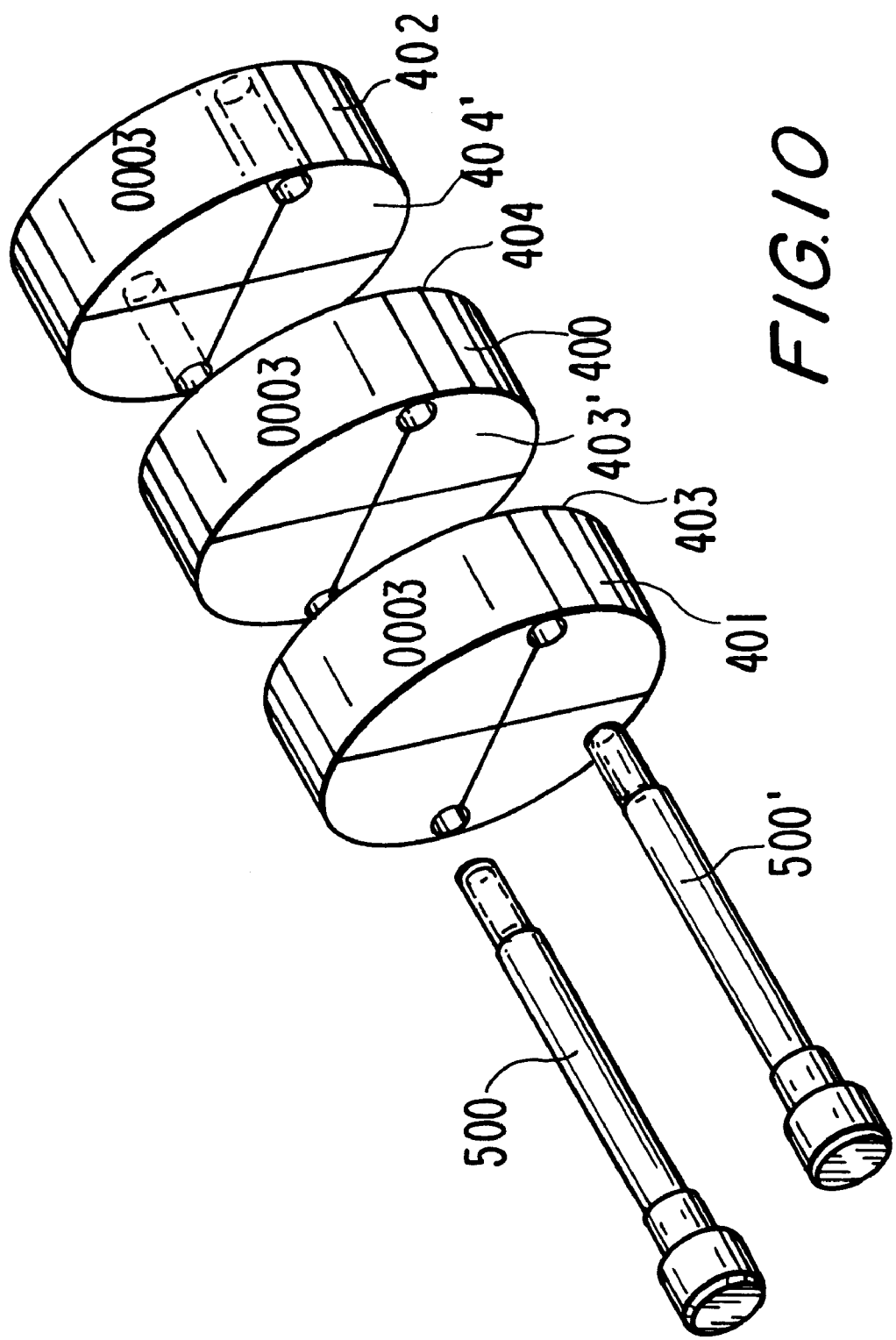
FIG. 10 is an exploded view of a third embodiment of an insert for the sample holder of FIGS. 5 through 7.

With this arrangement the ring 101 is loaded with the force which is introduced by the electromechanical transducer 9, while the housing 100, connected by the distance sensor 15 and the force sensor 12 with the connector part 50 of the adjusting device 13, can receive the reaction force. For this purpose, a three-part insert is provided having, viewed in the direction of the transverse axis, a central part and two lateral parts arranged on both sides of the central part. Different embodiments of this three-part insert are illustrated in FIGS. 8 through 10. In all of these embodiments the central part and the two lateral parts are cylindrical discs with circular end faces extending radially relative to the transverse axis.

FIG. 8 shows an exploded view of a first embodiment of the three-part insert in which the cylindrical disc 200 forming the central part is comprised of two partial disks 201, 202 which axially engage one another positive-lockingly with axial projections 203, 204 complementary to one another and recesses 205, 206 matching these projections and are clamped by axial threaded bolts 207.

The central area of the central disc 200 has an axially penetrating cutout 208 through which an axial bolt 209 passes with a spacing from the radial peripheral wall of the cutout 208. The bolt 209 is secured with its axial end in a disc 210 serving as a lateral part and with its opposite axial end is positive-lockingly received in an axial bore 211 of the disc 212 forming the other lateral part.

The bolt 209 is arranged diametrically to a location where the two partial disks 201, 202 with their axial projections 203, 204 with complementary shaping rests against one another. This location is in the form of an axially extending clamping gap. For this purpose, an eccentric 213 with an eccentric rod 214 acting in the direction of the clamping gap is supported in the partial discs 201, 202.

This insert is provided for strip or fiber-like samples which are wound about the bolt 209 and clamped with their ends with the aid of the eccentric rod 214 in the clamping gap. By a radial loading of the central disks 200 relative to the lateral discs 210, 212 in the direction of a straight line extending through the clamping gap and the bolt 209 the sample which is, for example, strip-shaped, is loaded with tension.

In the embodiment illustrated in FIG. 9 the central disc 300 is of a one-part configuration and formed with an axial through opening 301. An axial support beam 302 penetrates this through opening 301 with play and is secured with one axial end in the lateral disc 303 and with the other axial end is positive-lockingly supported in a receiving bore 304 of the other lateral disc 305. On the support beam 302 a support surface 306, oriented radially inwardly relative to the central disc 303, is provided for a preferably cylindrical sample. A support surface 308, formed by the end face of a radial plunger 307, is positioned opposite to the support surface 306 with radial spacing, wherein the plunger 307 is secured by a cylindrical shaft 309, extending radially from the support surface 308, in a radial bore 310 of the central disc 300 by means of an axially inserted clamping member 311.

In this insert, the sample is loaded with pressure between the two support surfaces 306, 308 when the central disc 300 is deflected relative to the lateral disks 303, 305 in a direction perpendicular to the support surfaces 306, 308.

In the embodiment of the insert illustrated in FIG. 10, the central disc 400 and the two lateral disks 401, 402 are substantially identical. Two identical samples are secured between the facing radial end faces 403, 403' and 404, 404' of the lateral disc 401 and the central disc 400, respectively, the central disc 400 and lateral disk 402, for example, by gluing. The sample is subjected to a shearing load by deflection of the central disc 400 relative to the two lateral discs 401, 402.

As is obvious from the above description, the inserts with samples arranged therein are inserted into the sample holder 11 such that the central disc 200, 300, 400, respectively, is positive-lockingly received in the ring 101 while the two lateral discs 210, 212 or 303, 305 or 401, 402 are positive-lockingly received in the cylindrical inlet areas 103, 103' of the housing 100, respectively. In this way, the central disc provides a holding part for a first area of the sample, respectively, via which the force generated by the transducer 9 is introduced, while the two lateral disks serve as holding parts, respectively, for a second area of the sample spaced from the first area with which the reaction force is supported.

In each of the embodiments of the insert illustrated in FIGS. 8 through 10, pairs of axially aligned bores are formed in the discs through which a pair of axial centering pins 500, 500' can be guided. For facilitating handling during the preparation of the insert and during insertion into the housing 100 with the ring 101 arranged therein, the centering pins 500, 500' can be guided through the axially aligned bores of the discs so that a stable cylindrical arrangement is obtained which can be easily handled. Of course, the centering pins 500, 500' must be removed during measuring.

While specific embodiments of the invention have been shown and described in detail to illustrate the inventive principles, it will be understood that the invention may be embodied otherwise without departing from such principles.

What is claimed is:

1. A device for dynamic-mechanical analysis of samples, the device comprising:
   a rigid support with uprightly aligned longitudinal axis;
   a sample holder, comprised of a first holder part and a second holder part, arranged in the rigid support;
   an electro-mechanical transducer mounted in the rigid support and configured to introduce a mechanical force corresponding to an electrical drive signal into the sample holder along a linear force transmission path parallel to the longitudinal axis;
   wherein the first and second holder parts are configured to be deflectable relative to one another along the force transmission path;
   wherein a first area of a sample is fastened to the first holder part and a second area of the sample, spaced from the first area of the sample, is fastened to the second holder part;
   wherein the mechanical force introduced by the transducer is coupled to the first holder part and the reaction force counteracting the mechanical force introduced by the transducer is supported on the second holder part;
   a measuring device configured to measure the deflection of the first and second holding parts relative to one another caused by the mechanical force introduced by the transducer;
   an adjusting device having a connector part connected to one end of the force transmission path and adjustable transverse to the longitudinal axis along a first spatial axis and along a second spatial axis extending perpendicularly to the first spatial axis;
   the adjusting device comprising a first carriage, configured to be slidable along the first spatial axis and having a first cylindrical guiding surface segment with a first cylinder axis extending parallel to the first spatial axis;
   the adjusting device further comprising a pivot frame seated slidably on the first cylindrical guiding surface segment; and
   the adjusting device further comprising a second carriage mounted on the pivot frame so as to be slidable along the second spatial axis on the pivot frame, wherein the second carriage has a second cylindrical guiding surface segment with a second cylinder axis parallel to the second spatial axis and the connector part is seated slidably on the second cylindrical guiding surface segment.

2. The device according to claim 1, wherein the first and second cylinder axes intercept one another.

3. The device according to claim 1, wherein the first and second guiding surface segments have identical radii of curvature.

4. The device according to claim 1, further comprising a stationary frame-shaped lower housing part having a first threaded spindle rotatably supported in the lower housing part, wherein the first carriage is slidably mounted on said lower housing part, and wherein the threaded spindle extends axially in the first spatial direction and engages a thread of the first carriage.

5. The device according to claim 4, wherein the first carriage has two opposite end faces extending transversely to the first spatial axis and wherein the first cylindrical guiding surface segment is formed by two circular disc segments provided on the two end faces of the first carriage, respectively, wherein the pivot frame is positioned between the two circular disc segments and has oppositely arranged end faces having recesses shaped complementarily to the two circular disc segments, respectively, wherein the recesses are supported on the circular disc segments.

6. The device according to one claim 5, wherein the pivot frame has a second threaded spindle rotatably supported in the pivot frame and extending axially in the second spatial direction, wherein the second threaded spindle engages a thread of the second carriage.

7. The device according to claim 6, wherein the second carriage has two end faces extending transversely to the second spatial direction and wherein the second cylindrical guiding surface segment is formed by two cylinder mantle segments formed on the two end faces of the second carriage, wherein the connector has gliding surfaces shaped complementarily to the cylinder mantle segments and is supported with the gliding surfaces on the cylinder mantle segments.

8. The device according to claim 6, wherein the first and second carriages and the pivot frame have cutouts and wherein the connector part has a projection extending in the direction of the longitudinal axis and penetrating through the cutouts of the first and second carriages and of the pivot frame.

9. The device according to claim 6, comprising a stationary upper housing part and a third threaded spindle rotatably supported in the upper housing part and extending axially in the second spatial direction, wherein the third threaded spindle has a first spindle thread and a first driver guided on the spindle thread, wherein the first driver engages the pivot frame.

10. The device according to claim 9, wherein a fourth threaded spindle is rotatably and axially slidably supported in the upper housing part, wherein the fourth threaded spindle extends axially in the first spatial direction and has a carriage driver coupled with the second carriage, wherein the fourth threaded spindle has a second spindle thread and a second driver guided on the second spindle thread, wherein the second driver engages the connector part.

11. The device according to claim 10, comprising indicator pins extending parallel to the first, second, third, and fourth threaded spindles, respectively, and connected to the first and second drivers and the first and second carriages guided on the threads of the threaded spindles, respectively.

12. A device for dynamic-mechanical analysis of samples, the device comprising:

a rigid support with uprightly aligned longitudinal axis;

a sample holder, comprised of a first holder part and a second holder part, arranged in the rigid support;

an electro-mechanical transducer mounted in the rigid support and configured to introduce a mechanical force corresponding to an electrical drive signal into the sample holder along a linear force transmission path parallel to the longitudinal axis;

wherein the first and second holder parts are configured to be deflectable relative to one another along the force transmission path;

wherein a first area of a sample is fastened to the first holder part and a second area of the sample, spaced from the first area of the sample, is fastened to the second holder part;

wherein the mechanical force introduced by the transducer is coupled to the first holder part and the reaction force counteracting the mechanical force introduced by the transducer is supported on the second holder part;

a measuring device configured to measure the deflection of the first and second holding parts relative to one another caused by the mechanical force introduced by the transducer;

an adjusting device having a connector part connected to one end of the force transmission path and adjustable transverse to the longitudinal axis along a first spatial axis and along a second spatial axis extending perpendicularly to the first spatial axis;

wherein the sample holder has a housing having a receiving chamber, extending through the housing along a transverse axis extending transversely to the longitudinal axis, and having a housing opening;

a ring arranged in the receiving chamber;

a three-part insert configured to be received in the receiving chamber, wherein the insert, when viewed in the direction of the transverse axis, has a central part forming the first holder part and lateral parts arranged on both sides of the central part and forming the second holder part;

a force transmission member connected to the transducer and the ring and extending through the housing opening into the housing in the direction of the longitudinal axis;

wherein the central part is supported positive-lockingly in the ring with movement play and the lateral parts are supported positive-lockingly in the receiving chamber;

wherein the housing has a connecting area positioned, when viewed along the longitudinal axis, opposite the housing opening, configured to be connected to the measuring device.

13. The device according to claim 12, wherein the central part and the two lateral parts are formed as cylindrical discs with circular end faces extending radially relative to the transverse axis.

14. The device according to claim 12, wherein the insert has a sample receiving chamber in the central part, a clamping gap extending from the sample receiving chamber radially outwardly relative to the transverse axis, and a rigid rod penetrating the sample receiving chamber in the direction of the transverse axis at a location spaced radially from the clamping gap, wherein the two lateral parts have recesses and wherein ends of the rod are supported in the recesses.

15. The device according to claim 12, wherein the insert has a sample receiving chamber in the central part, a support surface provided in the sample receiving chamber for supporting a sample radially relative to the transverse axis, and a counter abutment penetrating the receiving chamber in the direction of the transverse axis at a location radially spaced from the support surface, wherein the two lateral parts have recesses and wherein ends of the counter abutment are supported in the recesses of the two lateral parts.

16. The device according to claim 12, wherein the central part and the two lateral parts have centering bores aligned with one another in the direction of the transverse axis, wherein the housing has centering pins and wherein the centering pins are received in the centering bores.

17. A device for dynamic-mechanical analysis of samples, the device comprising:

a rigid support with uprightly aligned longitudinal axis;

a sample holder, comprised of a first holder part and a second holder part, arranged in the rigid support;

an electro-mechanical transducer mounted in the rigid support and configured to introduce a mechanical force corresponding to an electrical drive signal into the sample holder along a linear force transmission path parallel to the longitudinal axis;

wherein the first and second holder parts are configured to be deflectable relative to one another along the force transmission path;

wherein a first area of a sample is fastened to the first holder part and a second area of the sample, spaced from the first area of the sample, is fastened to the second holder part;

wherein the mechanical force introduced by the transducer is coupled to the first holder part and the reaction force counteracting the mechanical force introduced by the transducer is supported on the second holder part;

a measuring device configured to measure the deflection of the first and second holding parts relative to one another caused by the mechanical force introduced by the transducer;

an adjusting device having a connector part connected to one end of the force transmission path and adjustable transverse to the longitudinal axis along a first spatial axis and along a second spatial axis extending perpendicularly to the first spatial axis;

wherein the rigid support is a tubular body enclosing the force transmission path defined by the transducer, the sample holder, the measuring device, and the adjusting device, the tubular body having an access opening in the area of the sample holder.

18. The device according to claim 17, further comprising two tempering chamber halves in the area of the sample holder, wherein the two tempering chamber halves are slidable along a transverse axis, extending perpendicularly to the longitudinal axis, between a closed position, in which the two tempering chamber halves enclose the sample holder, and an open position, in which the sample holder is exposed.

19. The device according to claim 18, wherein the tempering chamber halves comprise two lateral arms supported on the tubular body.

* * * * *